United States Patent [19]

Miller et al.

[11] Patent Number: 5,312,410
[45] Date of Patent: May 17, 1994

[54] SURGICAL CABLE TENSIONER

[75] Inventors: David F. Miller, Eads, Tenn.; Leroy C. Bayliss, Sherwood, Ohio

[73] Assignee: Danek Medical, Inc., Memphis, Tenn.

[21] Appl. No.: 987,004

[22] Filed: Dec. 7, 1992

[51] Int. Cl.⁵ .......................... A61F 5/00; A61F 2/32
[52] U.S. Cl. .................................... 606/86; 606/103
[58] Field of Search ................ 606/86, 87, 88, 74, 606/103; 24/131 R, 26-29; 140/93 R, 93 A, 14, 22, 104, 105; 81/9.41, 9.42, 9.43, 315

[56] References Cited

U.S. PATENT DOCUMENTS

| 1,346,940 | 7/1920 | Collins. | |
|---|---|---|---|
| 2,049,361 | 7/1936 | Ericsson | 128/92 |
| 2,077,491 | 4/1937 | Perrelet | 81/9.1 |
| 2,291,413 | 7/1942 | Siebrandt | 606/103 |
| 2,622,460 | 12/1952 | Keeble | 81/9.3 |
| 3,254,680 | 6/1966 | Caveney | 140/93.2 |
| 3,645,302 | 2/1972 | Caveney et al. | 140/93.2 |
| 4,050,464 | 9/1977 | Hall | 128/303 |
| 4,587,963 | 5/1986 | Leibinger et al. | 128/92 |
| 4,966,600 | 10/1990 | Songer et al. | 606/74 |
| 5,057,113 | 10/1991 | Mingozzi | 606/103 |
| 5,163,940 | 11/1992 | Bourque | 606/103 |

FOREIGN PATENT DOCUMENTS

0532698  9/1931  Fed. Rep. of Germany.

Primary Examiner—Michael A. Brown
Attorney, Agent, or Firm—Woodard, Emhardt, Naughton, Moriarty & McNett

[57] ABSTRACT

This is an instrument for applying tension to a metal surgical cable used in certain surgical procedures. The cable tensioner has a ratchet feature which has the ability to steadily increase the tension in the cable. Also included is a scale incorporated into the cable tensioner so that the tension in the cable is directly measured and indicated at all times. Finally, the cable tensioner is ergonomically designed into an elongated cylindrical shape to easily fit in the cupped hand of a surgeon.

37 Claims, 5 Drawing Sheets

SURGICAL CABLE TENSIONER

BACKGROUND OF THE INVENTION

The present invention relates generally to a device for tensioning cable, and in particular, to a device for tensioning surgical cable in a variety of medical procedures.

Surgical cable is used in reconstructive spine surgery involving fusions, spine trauma surgery, total hip arthroplasty, fracture fixation, and other trauma surgery. Depending upon the application, the surgical cable can either be monofilament wire or a multifilament cable.

In a typical medical procedure in which surgical cable is utilized to secure two body parts together, a small permanent loop is made at one end of a length of surgical cable and held permanently by a tubular crimp member. The cable is wrapped around the two body parts and then the loose end of the cable is threaded through the permanent loop. A flanged tubular crimp member, sometimes referred to as a "tophat" because of its appearance, is threaded onto the loose end of the cable and slid down to abut the small loop. A cable tensioning device is then attached to the loose end of the cable. The tensioning device draws the cable through the small loop and tophat until the tension in the cable wrapped around the two body parts has achieved a desired amount. Next, the tophat is crimped in order to preserve the tension in the cable wrapped around the body parts and allow the cable tensioning device to be withdrawn. Finally, the loose cable extending from the crimped tophat is trimmed as necessary.

It is often desirable and usually critical that the tension in the surgical cable be ascertainable and controllable. Thus, it is desirable that the surgical tensioning device have the ability to tension the surgical cable in a controlled manner and afford the physician the ability to directly determine the tension in the cable at any time. In addition to these requisites, a usable surgical tensioning device should be designed in form and function to be ergonomic, easy to use, and reliable.

SUMMARY OF THE INVENTION

A surgical cable tensioner according to the present invention can comprise a housing having a distal end with a passageway sized to receive surgical cable therethrough. A ratchet member is movably connected to the housing, and means for gripping the surgical cable is mounted on the ratchet member. A cable route is defined between the distal end of the housing and the gripping means. Also, an extendable cable distance is defined by the distance along the cable route between the distal end of the housing and the gripping means. A manual means for ratcheting the ratchet member is attached to the housing and enables the cable distance to be extended to remove slack and raise the tension in the surgical cable. Finally, means for locking the ratchet member against movement with respect to the housing is attached to the housing and prevents the ratchet member from moving in a direction that shortens the cable distance. In the preferred embodiment, the surgical cable tensioner also includes a scale means attached to the cable tensioner which is capable of directly measuring and indicating the tension in the surgical cable.

One object of the present invention is to provide a surgical cable tensioner with an improved ergonomic design.

Another object of the present invention is to provide a surgical cable tensioner that directly measures and indicates the tension in the surgical cable at all times.

Another object of the present invention is to provide a surgical cable tensioner that includes a ratcheting action for raising tension in small predetermined steps.

Still another object of the present invention is to provide an improved surgical cable tensioner.

Other objects and advantages of the present invention will be apparent from the following description.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figures 1, 1A:
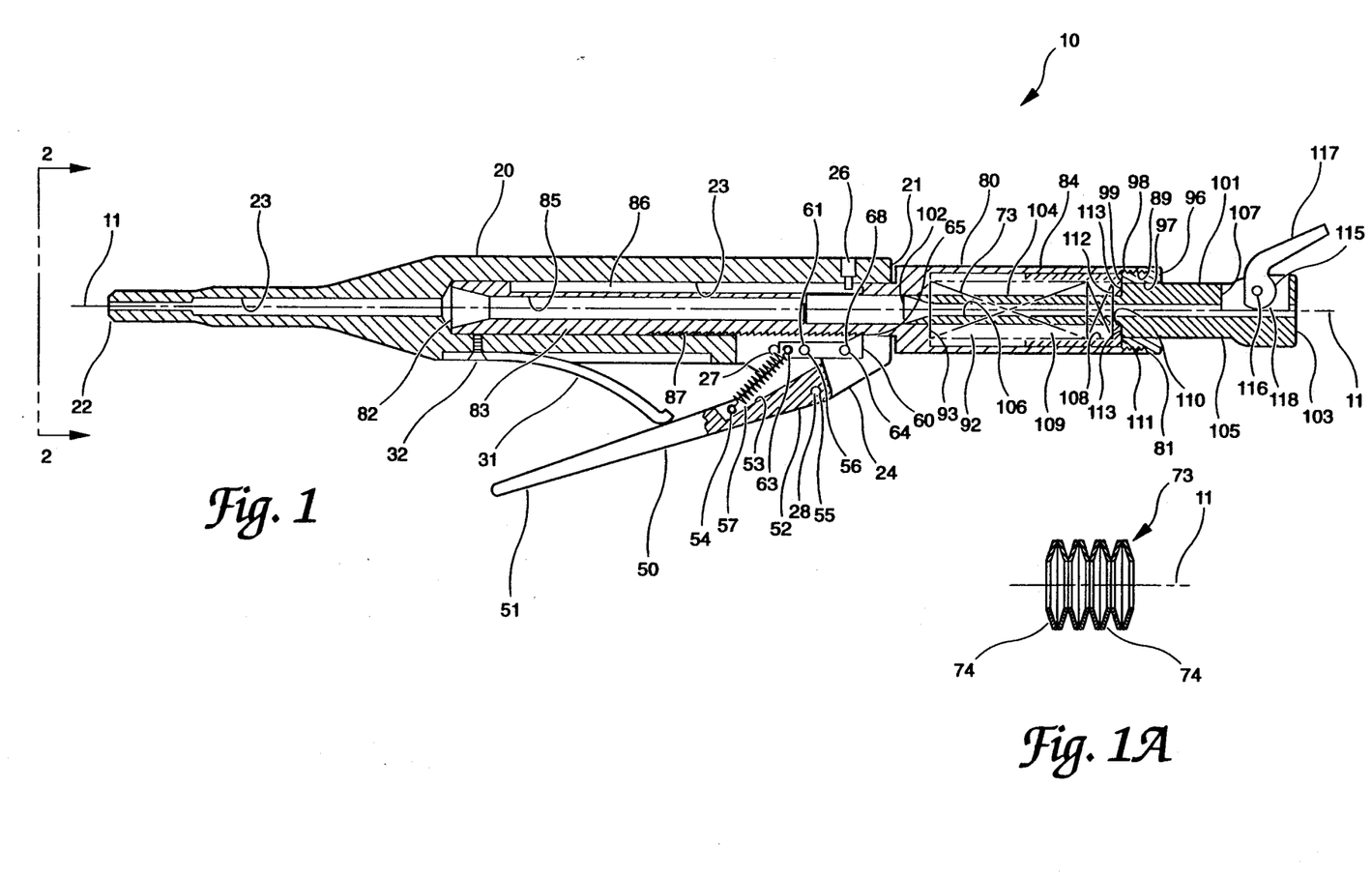
FIG. 1 is a side view in full section of a surgical cable tensioner according to the present invention.
FIG. 1A is a side view in full section of a portion of a stack of bellville washers utilized in the present invention.
Figure 4:
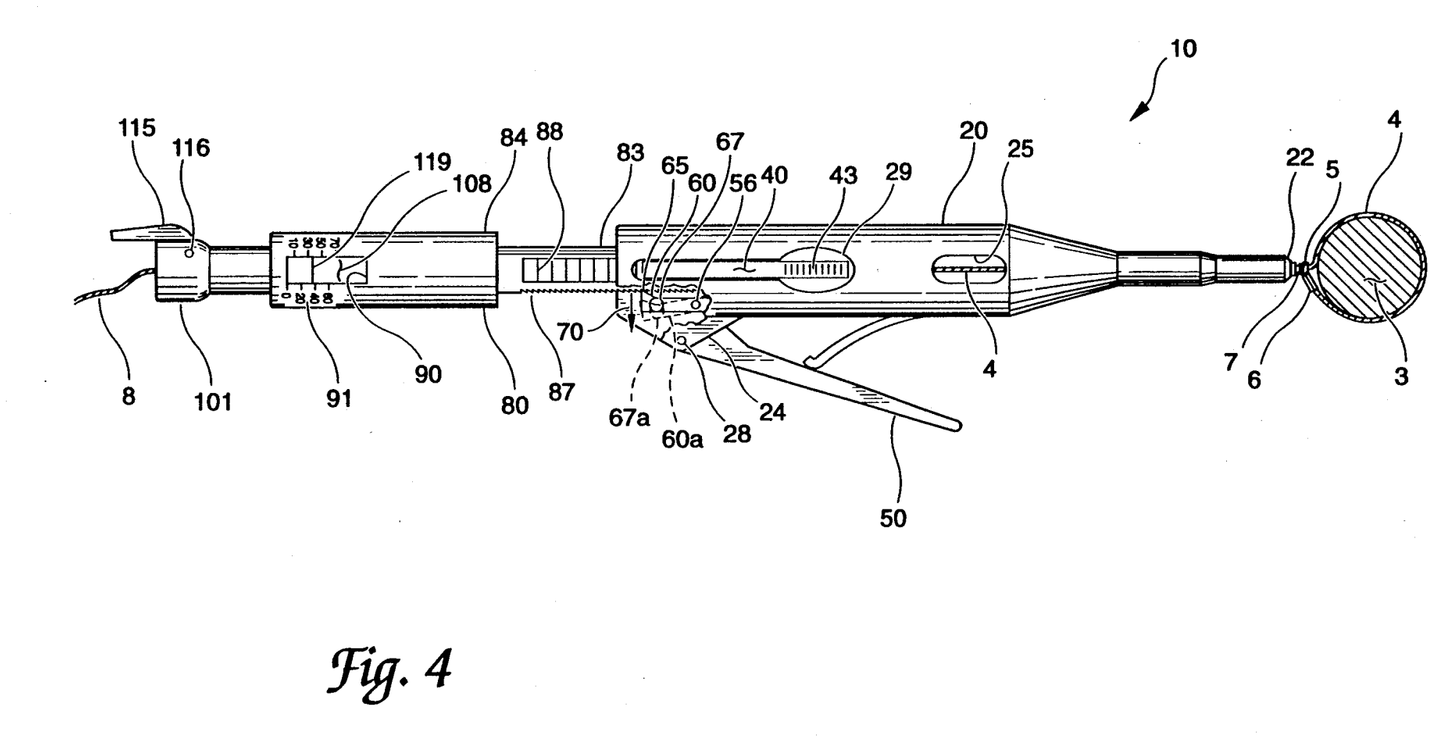
FIG. 4 is a side elevational view of the surgical cable tensioner of FIG. 1 looking in the direction of arrows 4—4 of FIG. 2.

Referring now to FIG. 1, the inner structure of a surgical cable tensioner 10 according to the preferred embodiment of the present invention is illustrated. Surgical cable tensioner 10 is built around a generally elongated stepped cylindrical housing 20 leaving a distal end 22 and a proximal end 21. Housing 20 is preferably cast in stainless steel and then machined into its final form. Housing 20 includes a stepped bore 23 that extends from distal end 22 through proximal end 21. At the bottom of the housing near the proximal end, a yoke is provided between a pair of housing walls 24 (see FIG. 2), for receiving and mounting other components of cable tensioner 10 to be described infra. The stepped bore 23 is generally symmetrical about centerline 11, which generally provides the working axis for cable tensioner 10. Referring to FIG. 4, housing 20 of cable tensioner 10 also includes opposing fenestration slots 25 which facilitate the complete sterilization of the interior of housing 20 during autoclaving.

A rack tube 80 has a distal end 82, and an intermediate portion which is slidably and fittingly received in the largest portion of bore 23 of housing 20. Rack tube 80 has a proximal end 81, which extends proximally (in a direction away from the distal end) from the proximal end 21 of housing 20. Telescoping portion 83 is received in stepped bore 23 and is capable of telescoping out of the proximal end 21 of the housing. A guide groove 86 (FIG. 3) is formed in the top of telescoping portion 83 of the rack tube 80. A guide pin 26 is attached to housing 20 and extends into groove 86 of rack tube 80 in order to prevent the rack tube from turning about centerline 11 with respect to housing 20. Like housing 20, the rack tube includes a cylindrical stepped passageway 85 that extends the complete length of the tube from distal end 82 through proximal end 81. Telescoping portion 83 of the rack tube also includes two toothed faces (racks) 87 and 88, with rack 87 on the bottom, and rack 88 on the side. Rack 87 provides the means by which the rack tube is telescopically ratcheted with respect to housing 20. Rack tube 80 is preferably cast in stainless steel and then machined into its final form.

Figure 2:
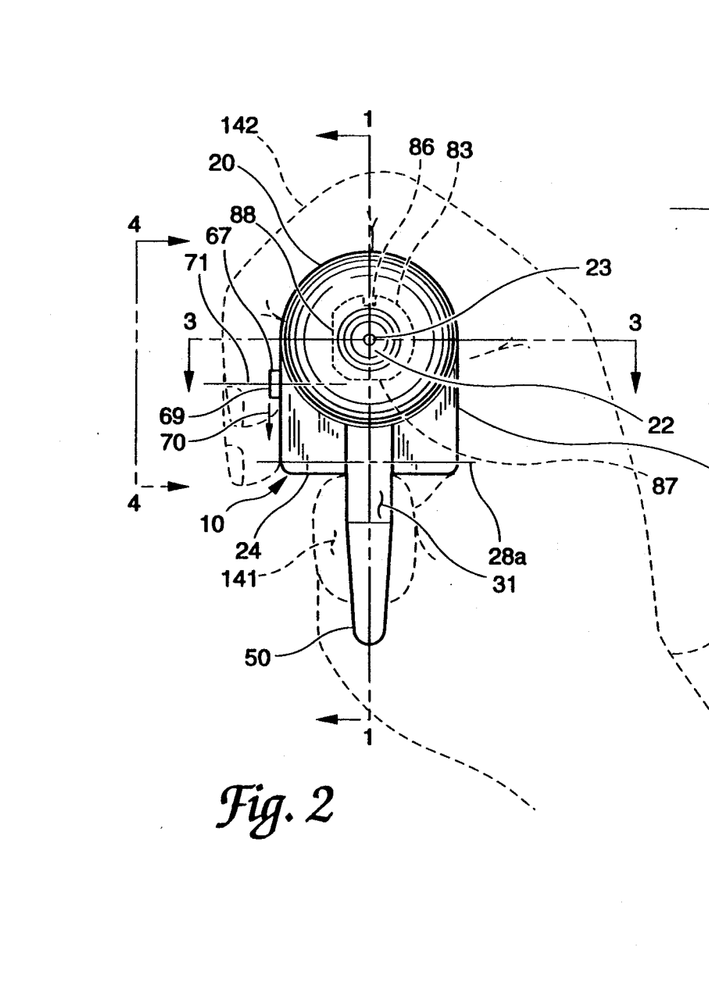
FIG. 2 is a distal end elevational view of the cable tensioner of FIG. 1.
Figure 6:
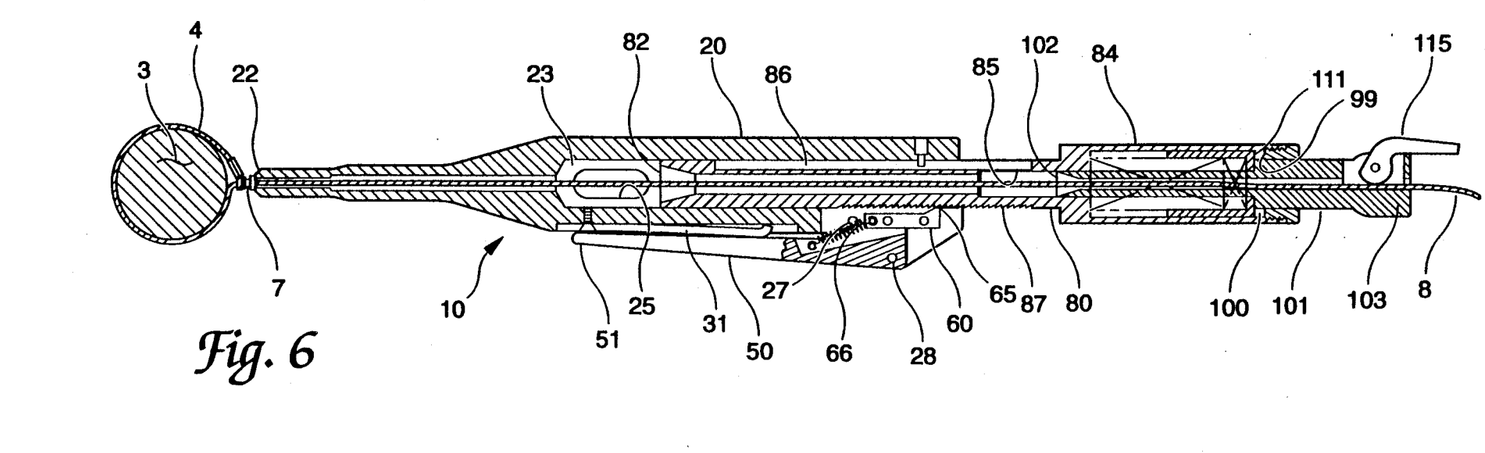

Rack tube 80 is telescopically ratcheted with respect to housing 20 by utilizing lever actuator 50 which is pivotally mounted between housing side walls 24. In particular, base 52 of lever actuator 50 includes a pivot bore 55 that receives lever pin 28 therethrough. Base 52 of lever actuator 50 substantially fills the space between housing side walls 24 (FIG. 2). The ends of lever pin 28 are mounted in side walls 24 such that lever actuator 50 is capable of pivoting about lever pin centerline 28a of FIG. 2. A lever return spring 31 is attached to housing 20 via screw 32 and serves to bias the tensioning handle portion 51 of lever actuator 50 to its extended position as shown in FIG. 1. Lever actuator 50 is pivoted about lever pin 28 simply by depressing handle portion 51 toward housing 20, as best shown in FIG. 6.

Base 52 of lever actuator 50 includes a groove 53 that is intercepted by a pair of axially aligned pivot bores (not shown) in the base, one on either side of groove 53. A pawl 60 is partially received within groove 53 and includes a pivot bore 61 that aligns with the above mentioned pivot bores in the base 52 of lever actuator 50. Pawl 60 is pivotally mounted to lever actuator 50 via a pawl attachment pin 56 whose ends are received within the pivot bores made on either side of groove 53 and pivot bore 61 of pawl 60. Thus, pawl 60 is pivotally mounted to lever actuator 50 by pin 56. A tension spring 57 is mounted between spring anchor pin 63 of pawl 60 and spring anchor pin 54 of lever actuator 50. Tension spring 57 biases tooth engagement surface 65 of pawl 60 into contact with rack 87 of rack tube 80. A backstop pin 27 is mounted between side walls 24 of housing 20 and serves as a backstop for pawl 60. Each depression of tensioning handle 51 causes pawl 60 to move parallel to centerline 11 in a direction toward proximal end 21 of housing 20. The action of lever actuator 50 and pawl 60 causes rack 80 to be telescopically moved with respect to housing 20. Both lever actuator 50 and pawl 60 are preferably machined from stainless steel.

The proximal portion of rack tube 80 consists of a cylindrical extension 84 defining a cylindrical cavity 92 slidably receiving a spring housing 108 therein. Spring housing 108 is cylindrically shaped and made from stainless steel. A portion of cylindrical extension 84 includes internal threads 89 adjacent the proximal end 81. An end cap 96, also made of stainless steel, has external threads 98 and is threadedly attached to threads 89 of rack tube 80. End cap 96 also includes a circular bore 97 therethrough that communicates with internal cavity 92 of cylindrical extension 84. The inner end 99 of end cap 96 serves as the means for maintaining spring housing 108 within cylindrical cavity 92. A compression spring means 73 is mounted within cylindrical cavity 92 between distal wall 93 of cylindrical extension 84 and inner wall 112 of spring housing 108, such that the end 111 of the spring housing is forced into abutting relationship with the end 99 of end cap 96. In the preferred embodiment, spring means 73 is a stack of bellville washers 74 as shown fragmentarily in FIG. 1A.

Cylindrical extension 84 of rack tube 80 includes at least one window 90 that opens onto the exterior surface of spring housing 108 as best shown in FIG. 4. Scale markings 91 in ten pound graduations up to approximately 70 pounds are made adjacent window 90. Spring housing 108 includes a reference mark 119 that moves when scale member 101 telescopically moves into cylindrical housing 84 of rack tube 80.

Scale member 101 has a distal end 102, which is slidably received in a portion of stepped bore 85 of rack tube 80, and a proximal end 103 that extends proximally out of end cap 96. Scale member 101 includes a spring pilot portion 104 that extends through bore 110 in the end of spring housing 108 and into cylindrical cavity 92. The stack of bellville washers 74 is mounted about pilot portion 104.

Scale member 101 also includes a telescoping portion 105 with a step inward to pilot portion 104 forming a shoulder 113 that abuts and is welded to spring housing end 111. In this way, scale member 101 and spring housing 108 move within cylindrical cavity 92 as a single unit. Bellville washers 74 bias scale member 101 to its extended position as shown in FIG. 1 wherein spring housing end 111 abuts against inner end 99 of end cap 96. Like housing 20 and rack tube 80, scale member 101 includes a cylindrical elongated passageway 106 that traverses the full length of scale member 101 from distal end 102 to proximal end 103. Also like the other parts, scale member 101 is made of stainless steel.

Figure 5:
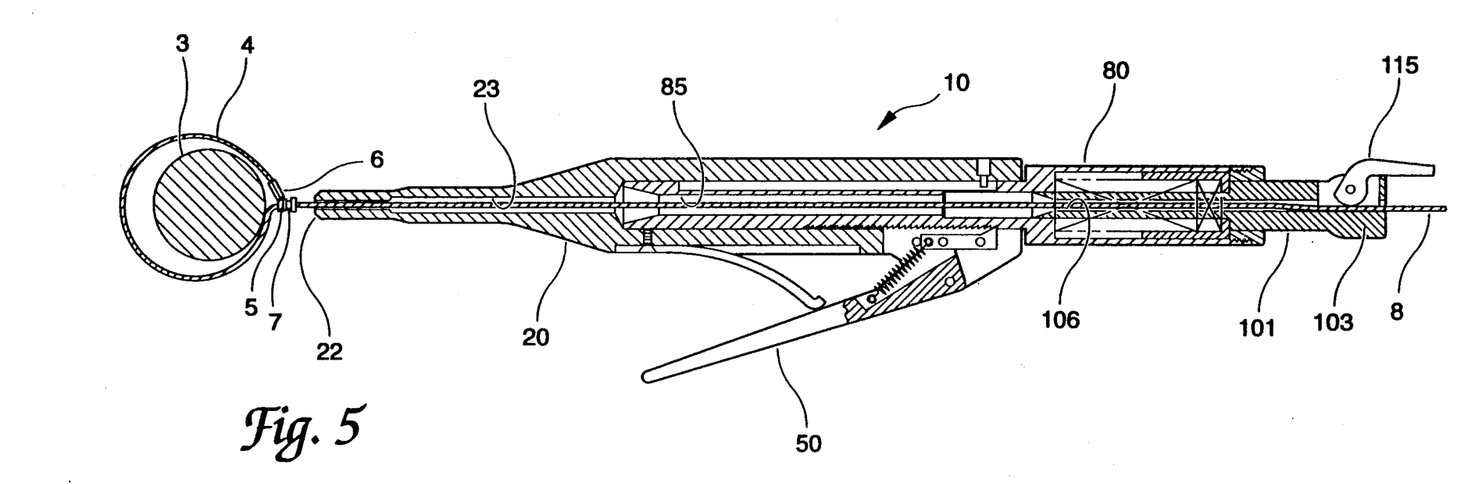
FIGS. 5-7 are a series of side views analogous to that of FIG. 1 and illustrating the action of the cable tensioner shown in FIG. 1.

A groove 107 adjacent the proximal end 103 of scale member 101 receives lever actuated cam 115 which is pivotally mounted on pivot pin 116 that spans the groove 107, the ends of the pin 116 being mounted in scale member 101. Groove 107 opens into passageway 106 such that gripping surface 118 of cam 115 can contact a surgical cable 4 (FIGS. 4-6) positioned in passageway 106. FIG. 1 shows cam 115 in its release position. Cam 115 is pivoted to its gripping position by depressing lever 117 to the position shown for instance in FIG. 5 such that a piece of surgical cable can be pinched between gripping surface 118 and the wall of passageway 106 as shown in FIG. 5.

Figure 3:
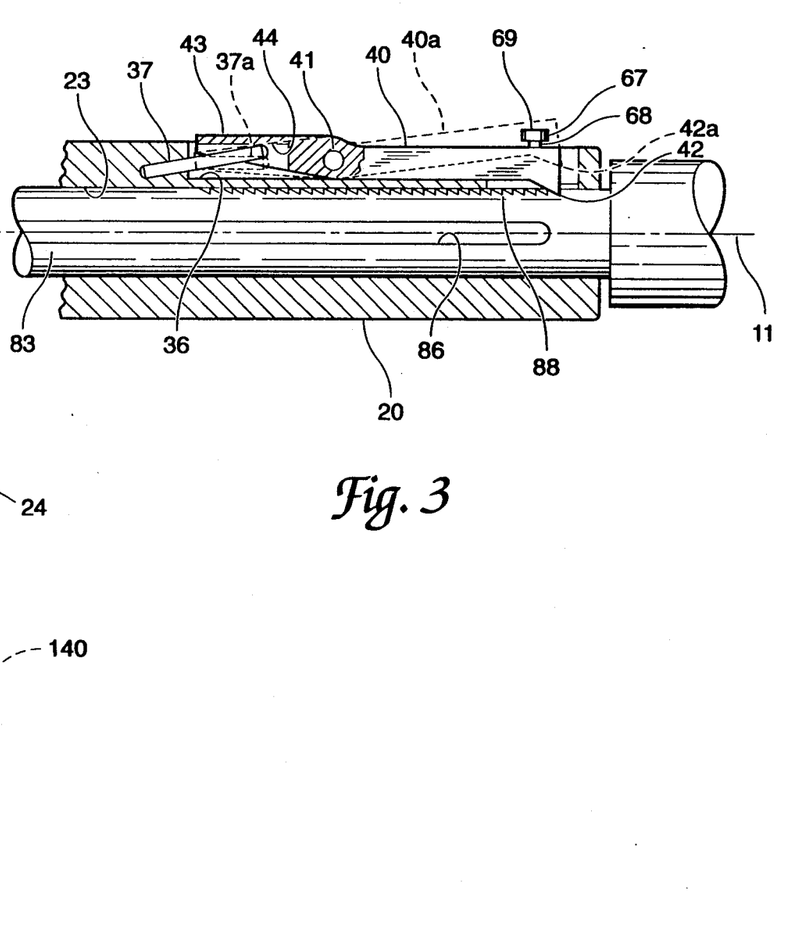
FIG. 3 is a partial top view of the ratchet rack tube of the cable tensioner, with other parts shown in section taken at line 3—3 of FIG. 2 and viewed in the direction of the arrows.

Referring now to FIG. 3, a rack lock 40 is provided and serves as one means for locking rack tube 80 against movement into housing 20. For this purpose, and in addition to the first rack 87, telescoping portion 83 of rack tube 80 also includes the second rack 88 arranged orthogonally with respect to first rack 87. In other words, it is on the side of the rack tube 80. An elongated groove 36 is cut into the side of housing 20 adjacent rack 88. An elongated rack lock 40 is pivotally mounted in groove 36 via pivot pin 41, which spans groove 36 and whose ends are mounted in the walls of groove 36. Thus, rack lock 40 can pivot between a locked position in which tooth engagement surface 42 engages the teeth of rack 88, and a release position illustrated in broken lines as 40a in FIG. 3. The proximal end of groove 36 opens into bore 23 of housing 20 such that tooth engagement surface of rack lock 40 can engage the teeth of rack 88. A cavity at the rear end of rack lock 40 provides a spring guide surface 44 that receives a portion of lock return spring 37, which is preferably a short segment of spring wire or rod. Spring 37 is snug fit in a socket in the end wall of groove 36 as shown in FIG. 3. Because the other end of spring 37 rests against the surface of spring guide 44, rack lock 40 is naturally urged to its locked position. However, rack lock 40 can be moved to its release position by depressing release surface 43 into oval cutout 29 (FIG. 4) of housing 20 toward axis 11 such that return spring 37, rack lock 40 and tooth engagement surface 42 are moved to their release positions designated respectfully as 37a, 40a and 42a.

As previously described, pawl 60 (FIG. 1) normally prevents rack tube 80 from telescoping into housing 20. This is accomplished because tension spring 57 normally urges tooth engagement surface 65 of pawl 60 into engagement with the teeth of rack 87. In order to move rack tube 80 telescopically into housing 20 from an extended position as shown for instance in FIG. 4, both rack lock 40 and pawl 60 must be disengaged from their respective cooperating toothed surfaces or racks 88 and 87 on the rack tube 80. As discussed earlier, rack lock 40 is moved to its release position simply by depressing release surface 43. With regard to pawl 60, a pawl release pin 67 includes a head portion 69 and a shaft 68 which extends through a slot (not shown) in one of the housing side walls 24 and is press-fitted in a hole 64 of pawl 60. When head 69 of pawl release pin 67 is pushed down in the direction of arrow 70 (FIGS. 2 and 4), the tooth engagement surface 65 of pawl 60 is pushed away from rack 87 of rack tube 80. Thus, rack tube 80 can only be telescoped into housing 20 from its extended position as shown in FIG. 4 to its concealed position as shown for instance in FIG. 1 by releasing both rack lock 40 and pawl 60 simultaneously. The release action of pawl 60 is illustrated in FIG. 4 wherein pawl 60 is shown by broken lines 60a as having been moved down in the direction of arrow 70 to its release position by manually moving pawl release pin 67 down in the direction of arrow 70 to the position shown in broken lines 60a and 67a, respectively.

Operation of the Cable Tensioner

Housing 20 preferably has a diameter on the order of about ⅜ inch so that cable tensioner 10 can be easily cupped in a physician's hand as shown in broken lines in FIG. 2. In this way, the physician's thumb 141 is naturally positioned adjacent lever actuator 50. Also, the physician's fingers 142 are positioned adjacent pawl release pin head 69 and rack lock 40. This ergonomic arrangement allows the physician to easily ratchet the rack tube with respect to the housing by repeatedly depressing lever actuator 50 with his or her thumb 141. Furthermore, the physician's fingers 142 of hand 140 are conveniently close to the lock release mechanisms of the device so that rack tube 80 can be released with respect to housing 20 while maintaining a capped grip on cable tensioner 10.

In preparing the cable tensioner 10 of the present invention for use, both rack lock 40 and pawl 60 are manually moved to their release positions when the cable tensioner is in an upright (axis 11 vertical) position so that telescoping portion 83 of rack tube 80 simply slides under the action of gravity into housing 20 to a position as shown in FIG. 1. Surgical cable 4 is made ready by first forming a small permanent loop 5 on one end utilizing a crimp 6. Next, surgical cable 4 is wrapped around the body part or parts 3 and the loose end 8 of cable 4 is threaded through the loop 5. A tophat type crimping member 7 is then threaded over the loose end 8 of surgical cable 4 and into abutting relation with loop 5. Loose end 8 of cable 4 is then threaded into bore 23 of housing 20 beginning at distal end 22. Loose end 8 is then advanced into bore 85 of rack 80 and finally through bore 106 of scale member 101 until a portion of loose end 8 extends proximally out of the proximal end 103 of scale member 101. Then the distal end 22 of the housing is pushed against the crimp 7. Then cam 115 is moved from its release position to its gripping position as shown in FIG. 5 so that the loose end 8 of cable 4 is secured to scale member 101. The physician then pulls on the proximal end 103 of scale member 101 to remove any excess slack from surgical cable 4. In so doing, rack 80 is telescoped out to a partially extended position as shown in FIG. 6 and locked in place via both rack lock 40 and pawl 60. Pulling proximal end 103 of scale member 101 causes the distal end 22 of housing 20 to abut and remain securely against tophat 7 when all the slack in cable 4 is removed and the rack tube is locked.

A cable route is defined between distal end 22 of housing 20 and cam 115. The tension in surgical cable 4 is increased by increasing the cable distance along the cable route, which is accomplished by telescoping rack tube 80 outward with respect to housing 20. Tension is built up into surgical cable 4 by ratcheting rack tube 80 with respect to housing 20 using lever actuator 50. Each depression of lever actuator 50 causes the rear end 66 of pawl 60 to move away from back stop 27 in the direction of cam 115 until rack lock 40 clicks into its next successive tooth (FIG. 6). Lever actuator 50 is then allowed to spring back to its extended position under the force of lever return spring 31. Successive teeth of racks 88 and 87 of rack tube 80 are preferably on the order of about 0.062 inches apart. Thus, with each depression of lever actuator 50, rack tube 80 telescopes out of housing 20 a distance corresponding to one tooth length, or about 0.062 inches.

Figure 7:
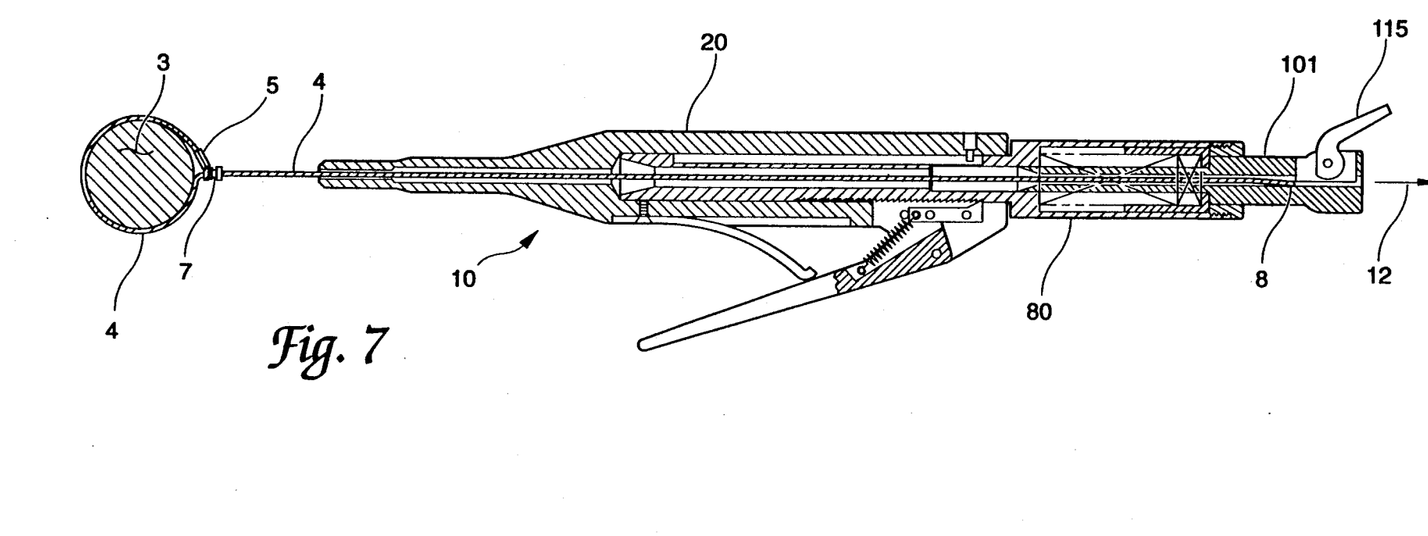

As tension is increased in surgical cable 4, scale member 101 begins to slide in the bore 92 of cylindrical extension 84 of rack tube 80 thereby compressing bellville washers 74 and moving wall 111 away from end cap 96, as best shown in FIG. 6. Viewed from the outside of the device (FIG. 4), reference marker 119 begins moving with respect to scale markings 91 directly indicating the tension in surgical cable 4. Of course, bellville washers 74 (FIG. 1A) must be properly calibrated so that the tension scale is accurate. FIG. 4 shows the surgical cable 4 having approximately 40 pounds of tension while FIG. 6 illustrates the device when only about 10 pounds of tension has been induced into surgical cable 4. After cable tensioner 10 has been ratcheted to produce the desired amount of tension in surgical cable 4, the physician crimps tophat 7 onto cable 4 utilizing a separate crimping device. Then, the cable tensioner is no longer needed so the physician simply moves cam 115 to its release position and withdraws cable tensioner 10 away from tophat 7 in the direction of arrow 12 shown in FIG. 7. Finally, the physician trims the excess portion of surgical cable 4 that is extending away from tophat 7.

It should be pointed out that although the embodiment illustrated utilizes a telescoping ratchet member (rack), a cogged wheel and capstan could be substituted for rack tube 80. In such an alternative, the cogged capstan would be ratcheted to wind the excess surgical cable onto the capstan in order to raise the tension in the cable. In such a case, the "cable route" defined in the claims would spirally wrap around the capstan, instead of the purely straight cable route shown in the preferred embodiment that is illustrated. Also, the "cable distance" defined in the claims would include a spiral portion at the capstan which distance would be increased by ratcheting the capstan to wind more cable thereon. In another contemplated variation, a torsional scale could be substituted for the linearly reciprocating scale that is illustrated. In such a case, a torsional spring could be calibrated to directly reveal the pound tension in the surgical cable as in the illustrated embodiment.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A surgical cable tensioner comprising:
   a housing leaving a distal end for reference to a point on a surgical cable, and a passageway sized to receive surgical cable therethrough;
   a ratchet member movably connected to said housing;
   means, mounted on said ratchet member, for gripping surgical cable;
   a cable route being defined between said distal end of said housing and said gripping means;
   an extendable cable distance being defined by the distance along said cable route between said distal end of said housing and said gripping means;
   manual means, attached to said housing, for ratcheting said ratchet member to extend said cable distance; and
   means, attached to said housing, for locking said ratchet member against movement with respect to said housing in a direction that shortens said cable distance.

2. The surgical cable tensioner of claim 1 wherein said cable route extends through said housing.

3. The surgical cable tensioner of claim 2 wherein said housing is fenestrated to better facilitate complete sterilization thereof.

4. The surgical cable tensioner of claim 2 wherein said housing is elongated and substantially cylindrical with a diameter sized to permit said housing to be cupped in a human hand and arranged so that said manual ratcheting means is adjacent the thumb of the cupped hand.

5. The surgical cable tensioner of claim 4 wherein said manual ratcheting means includes a lever actuator pivotally mounted on said housing and extending toward said distal end such that thumb movement toward and away from said housing by the cupped hand actuates said manual ratcheting means.

6. The surgical cable tensioner of claim 5 wherein said lever actuator is spring biased to return to a position extending away from said housing.

7. The surgical cable tensioner of claim 1 wherein said ratchet member includes a rack with a plurality of teeth on one side; and
   said manual ratcheting means includes a pawl engageable with said teeth of said rack and a lever actuator pivotally mounted to said housing and attached to said pawl; and
   wherein pivoting said lever actuator ratchets said rack to move with respect to said housing to extend said cable distance.

8. The surgical cable tensioner of claim 7 wherein said cable route extends through said rack; and
   said gripping means is a cam pivotally mounted on said ratchet member and pivotable between a gripping position and a release position.

9. The surgical cable tensioner of claim 8 wherein said rack is telescopically movable with respect to said housing.

10. The surgical cable tensioner of claim 1 further comprising scale means, mounted on said ratchet member, for directly measuring and indicating the amount of tension in the surgical cable being tensioned.

11. The surgical cable tensioner of claim 10 wherein said scale means includes a scale member movably mounted to said ratchet member and scale markings on said scale member and said ratchet member, said scale member being biased to a zero position but being capable of moving away from said zero position a distance proportional to the tension in the surgical cable, said scale indicating the distance that said scale member is away from said zero position; and
    said gripping means is attached to said scale member.

12. The surgical cable tensioner of claim 11 wherein said scale member is biased to said zero position by a stack of bellville washers positioned between said scale member and said ratchet member.

13. The surgical cable tensioner of claim 1 further comprising secondary means, attached to said housing, for locking said ratchet member against movement with respect to said housing in a direction that shortens said cable distance.

14. The surgical cable tensioner of claim 13 wherein said secondary locking means includes a lock member pivotally mounted on said housing and pivotable between a locking position and a release position.

15. The surgical cable tensioner of claim 14 wherein said lock member is spring biased to said locking position but manually pivotable to said release position.

16. A surgical cable tensioner comprising:
    a housing having a distal end with a passageway sized to receive surgical cable therethrough;
    a scale member movably mounted to said housing;
    means, attached to said scale member, for gripping surgical cable;
    a cable route being defined between said distal end of said housing and said gripping means;
    an extendable cable distance being defined by the distance along said cable route between said distal end of said housing and said gripping means;
    spring means, mounted between said scale member and said housing, for biasing said scale member to a zero position with respect to said housing, said scale member being movable away from said zero position a distance proportional to the tension in the surgical cable;
    scale means for indicating how far said scale member is away from said zero position;
    means for moving said gripping means with respect to said housing to extend said cable distance; and
    means for locking said gripping means against movement with respect to said housing in a direction that shortens said cable distance.

17. The surgical cable tensioner of claim 16 wherein said cable route extends through said housing.

18. The surgical cable tensioner of claim 17 wherein said housing is fenestrated to better facilitate complete sterilization thereof.

19. The surgical cable tensioner of claim 17 wherein said housing is elongated and substantially cylindrical with a diameter sized to permit said housing to be cupped in a human hand and arranged so that an actuator portion of said moving means is adjacent the thumb of the cupped hand.

20. The surgical cable tensioner of claim 19 wherein said moving means is a manual ratcheting means that includes a lever actuator pivotally mounted on said housing and extending toward said proximal end such that thumb movement toward and away from said housing by the cupped hand actuates said manual ratcheting means.

21. The surgical cable tensioner of claim 20 wherein said lever actuator is spring biased to return to a position extending away from said housing.

22. The surgical cable tensioner of claim 16 further comprising secondary means, attached to said housing, for locking said gripping means against movement with respect to said housing in a direction that shortens said cable distance.

23. The surgical cable tensioner of claim 22 wherein said secondary locking means includes a lock member pivotally mounted on said housing and pivotable between a locking position and a release position.

24. The surgical cable tensioner of claim 23 wherein said lock member is spring biased to said locking position but manually pivotable to said release position.

25. The surgical cable tensioner of claim 16 further comprising a ratchet member movably mounted between said housing and said scale member; and
said moving means is a manual ratcheting means for ratcheting said ratchet member to move with respect to said housing to extend said cable distance.

26. The surgical cable tensioner of claim 25 wherein said ratchet member is a rack tube with a plurality of teeth on one side; and
said manual ratcheting means includes a pawl engageable with said teeth and a lever actuator pivotally mounted to said housing and attached to said pawl; and
wherein pivoting said lever actuator ratchets said rack tube to move with respect to said housing to extend said cable distance.

27. The surgical cable tensioner of claim 26 wherein said cable route extends through said rack tube; and
said gripping means is a cam pivotally mounted on said ratchet member and pivotable between a gripping position and a release position.

28. The surgical cable tensioner of claim 27 wherein said rack tube is telescopically movable with respect to said housing.

29. The surgical cable tensioner of claim 16 wherein said scale member is biased to said zero position by a stack of bellville washers positioned between said scale member and said ratchet member.

30. A surgical cable tensioner comprising:
an elongated substantially cylindrical housing having a distal end and a passageway extending therethrough;
a rack tube telescopically mounted in said housing and having a rack thereon and having a passageway extending therethrough in communication with said passageway of said housing;
a scale member telescopically mounted in said passageway of said rack tube and having a passageway extending therethrough in communication with said passageway of said rack tube;
means, attached to said scale member, for gripping surgical cable;
spring means, mounted in said passageway of said rack tube, for biasing said scale member to a zero position, said scale member being movable away from said zero position a distance proportional to the tension in a surgical cable being tensioned;
a scale marked on said ratchet member and said scale member for indicating how far said scale member is away from said zero position;
an extendable cable distance defined between said distal end of said housing and said gripping means;
manual means, attached to said housing, for ratcheting said ratchet member to telescopically move with respect to said housing thereby extending said cable distance; and
means, attached to said housing, for locking said ratchet member against movement with respect to said housing in a direction that shortens said cable distance.

31. The surgical cable tensioner of claim 30 further comprising secondary means, attached to said housing, for locking said ratchet member against movement with respect to said housing in a direction that shortens said cable distance.

32. The surgical cable tensioner of claim 31 wherein said secondary locking means includes a lock member pivotally mounted on said housing and pivotable between a locking position and a release position.

33. The surgical cable tensioner of claim 32 wherein said lock member is spring biased to said locking position but manually pivotable to said release position.

34. The surgical cable tensioner of claim 30 wherein said manual ratcheting means includes a lever actuator pivotally mounted on said housing and extending toward said proximal end such that thumb movement toward and away from said housing by the cupped hand actuates said manual ratcheting means.

35. The surgical cable tensioner of claim 34 wherein said lever actuator is spring biased to return to a position pivoted away from said housing.

36. The surgical cable tensioner of claim 30 wherein said gripping means is a cam pivotally attached to said scale member and pivotable between a gripping position and a release position.

37. The surgical cable tensioner of claim 30 wherein said scale member is biased to said zero position by a stack of bellville washers positioned between said scale member and said ratchet member.

* * * * *